United States Patent [19]

Banko

[11] 4,167,944
[45] Sep. 18, 1979

[54] ROTATABLE SURGICAL CUTTING INSTRUMENT WITH IMPROVED CUTTER BLADE WEAR

[75] Inventor: Anton Banko, Bronx, N.Y.

[73] Assignee: Surgical Design Corp., Long Island City, N.Y.

[21] Appl. No.: 810,399

[22] Filed: Jun. 27, 1977

[51] Int. Cl.² ............................................ A61B 17/32
[52] U.S. Cl. .................................. 128/305; 128/752; 128/6; 128/276
[58] Field of Search .................. 128/305, 276, 2 B, 6; 30/240, 133, 41.5

[56] References Cited

U.S. PATENT DOCUMENTS

| 3,732,858 | 5/1973 | Banko | 128/2 B |
|---|---|---|---|
| 3,945,375 | 3/1976 | Banko | 128/6 |

Primary Examiner—Robert W. Michell
Assistant Examiner—Michael H. Thaler
Attorney, Agent, or Firm—Darby & Darby

[57] ABSTRACT

A cutter body for a surgical instrument having at least one blade surface thereon which rotates relative to a fixed blade surface. The cutter body is shaped to minimize the stress and wear of the rotatable cutter blade.

22 Claims, 6 Drawing Figures

ROTATABLE SURGICAL CUTTING INSTRUMENT WITH IMPROVED CUTTER BLADE WEAR

In my prior U.S. Pat. No. 3,945,375 granted Mar. 23, 1976, as well as the various patents referred to therein, a surgical instrument is disclosed of the type having a rotating cutter with a blade which moves relative to a stationary cutting surface to produce a shearing action. The instrument is disclosed as being used for microsurgery applications, such as operating in or on the eye, where it is to be inserted into the eye to remove tissue from a body.

The rotating portion of the cutter of U.S. Pat. No. 3,945,375 is of generally trunco-conical shape and formed with a pair of helical cutting flutes spaced 180° apart. Each flute has a cutting blade surface. The rotatable cutter is mounted at the end of a shaft which is uged forward in the tip of the instrument by the force of a spring. There is a zero clearance between the inside of the tip and the blades so that the net result is a controlled self-sharpening action as the blades wear and are moved forward in the tip.

The present invention is directed to improvements in cutters of the aforementioned types of instruments. In accordance with the invention, a trunco-conical cutter body is provided with a pair of flutes thereon which are spaced 180° apart. The surface of the blades decreases in width from the rear of the cutter body, where the cutting body is supported, toward its front, where the active cutting area is located. This arrangement provides a stress distribution thereby controlling and reducing the wear at the active cutting area. The arrangement also permits locating the active cutting area closer to the tip of the instrument.

It is therefore an object of the present invention to provide an instrument for removing tissue from a portion of a body.

An additional object is to provide an instrument for removing material from a body in which a probe is to be inserted into the body, the instrument including a rotatable fluted cutter.

Another object is to provide an instrument for removing tissue from a body in which the instrument brings tissue into a cutting relationship with a rotatable cutter.

A further object is to provide an instrument with a rotatable cutter blade in which blade wear is minimized and controlled.

An additional object is to provide a cutter body for an instrument having a blade supporting region and a cutting region in which the width of the blade decreases from the supporting to the cutting region.

Another object is to provide a cutter body for an instrument having a supporting region and a cutting region in which a portion of the body is adapted for controlled wear.

Other objects and advantages of the present invention will become more apparent upon reference to the following specifications and annexed drawings, in which.

Figure 1:
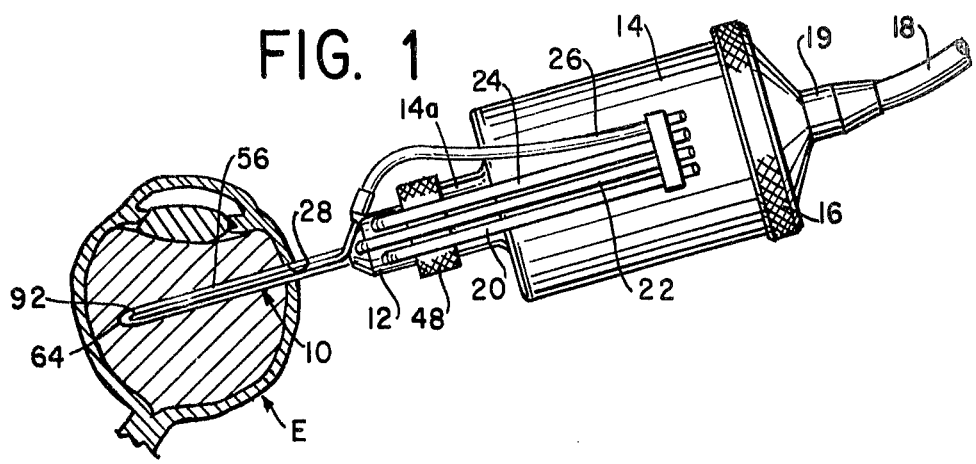
FIG. 1 is an overall plan view of the instrument shown for use in performing an operation in the eye.

Referring to FIG. 1, the instrument includes a probe extending from a fluid supply cup 12 which in turn is attached to a motor housing 14. The housing 14 contains a conventional electric motor (not shown) and is closed off by a cap 16 which is threaded and otherwise sealed to the main housing 14. Cable 18 extends through a grommet 19 in the cap 16 to supply current to the motor. A suitable switching circuit (not shown) for the motor can be provided at a location remote from the instrument.

Extending outside the housing, and attached to the housing if desired, are three fluid flow conduits 20, 22 and 24. These conduits respectively provide evacuation flow, irrigation fluid and a reverse flow fluid through cup 12 to the probe 10 in a manner to be described. An optical rod, or bundle of optic fibers 26, is also shown attached to the probe 10.

The probe 10 is shown in FIG. 1 inserted through an opening 28 in the eye E. The probe 10 has located therein a cutter (not shown in FIG. 1) which is adapted to cut tissue from within the eye. The cut tissue is removed via the evacuation conduit 20. It should be understood, of course, that the instrument can be used at any body location of a human or animal.

Figure 2:
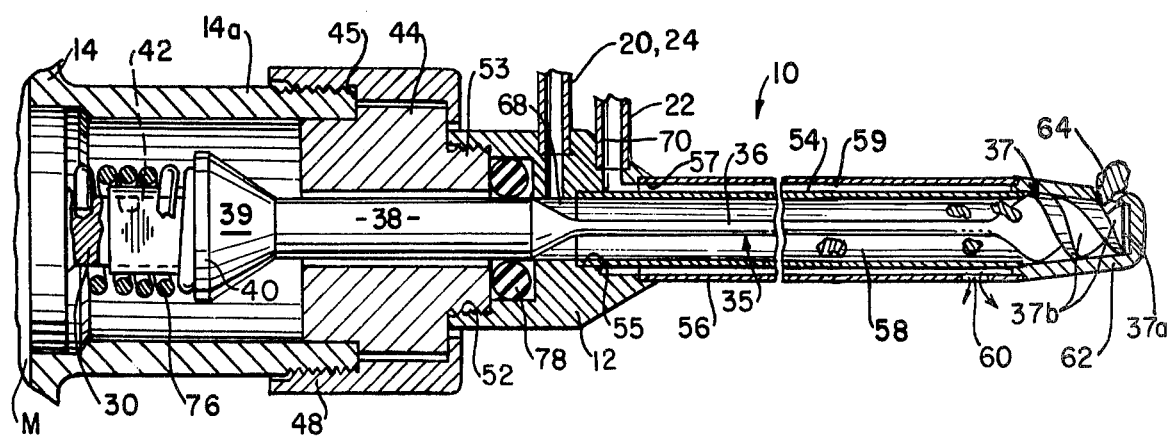
FIG. 2 is a cross-sectional view of a portion of the instrument showing the details thereof.

FIG. 2 shows the details of the instrument. The motor housing 14 contains the motor M which has an output shaft 30 extending into a neck 14a on the housing. The instrument has a cutting tool 35 which includes a shaft 36, a fluted drill type cutter 37, and a shank 38 whose end is fastened to a holder 39 having a shoulder 40. Holder 39 has a partial internal bore 42 which fits over the motor shaft 30.

The cutting tool shank 38 fits in a bushing 44 having a shoulder 45 which is held against the end of neck 14a by a collar 48 threaded onto housing neck 14a.

The fluid supply cup 12 is threaded at 52 onto a shoulder 53 on bushing 44. A pair of tubular shells 54 and 56 are mounted on internal steps 55 and 57 on the front end of the cup 12. Inner shell 54 defines a central flow passage for evacuation flow and reverse fluid flow while the space between shells 54 and 56 defines a passage 59 for the flow of irrigation fluid. The irrigation fluid exits through an opening 60 located near the end of the outer shell 56.

The front ends of both shells 54 and 56 are sealed off by a nose cone 62 of truncated conical shape. The shells 54, 56 and the cone 62 are made of a suitable biologically inert metal material, such as stainless steel, so the cone can be welded to the shells. The nose cone 62 has an opening 64 at a selected position along its length. The opening 64 is of generally circular shape and has an inwardly tapering wall 65. The lower edge of wall 65 is sharpened to form a cutting edge. In the embodiment of FIGS. 1 and 2 opening 64 is preferably disposed 180° from the irrigation fluid opening 60.

Cup 12 is formed with a first stepped bore 68 into which the fluids from both conduits 20 and 24 are applied. It is preferred that the two conduits 20 and 24 be connected together by a suitable T fitting (not shown) external to probe 10 and a common outlet conduit inserted in bore 68. The outlet of the bore 68 communicates with the interior passage 58 of the probe so that the passage can receive both evacuation and reverse flow-fluids. Similarly, cup 12 is formed with a second bore 70 to accept and hold the irrigation fluid conduit 22. The bore 70 communicates with the passage 59 between shells 54 and 56 and the fluid exits out of the outlet opening 60.

The evacuation force for conduit 20 causing the evacuation flow is produced by any suitable means. A constant displacement type pump can be used to produce the evacuation. The irrigation fluid for conduit 22 and the reverse flow fluid for conduit 24 are preferably sterile solutions, for example, saline solutions of the same or different salinity.

The cutter 37 of cutting tool 35 is urged toward the inner surface of the front end of the nose cone 62 by a spring 76 which acts between the end of the motor 14 and the shoulder 40 of key 39. Thus, a force is always exerted forwardly and longitudinally of the axis of tool 35. An O-ring 78 is placed over shank 38 in cup 12 between a shoulder of the cup terminating the passage through which the cutter extends and the bushing neck 53. This seals off fluid between bore 68 and the motor housing 14, and the atmosphere.

The cutter tool shaft 36 between the shank 38 and the cutter 37 is preferably of a material which has some degree of flexibility or elasticity. For example, it has been found that stainless steel is a satisfactory material having a dimension, for example, of 0.022 inch. The flexibility of shaft 36 and the use of spring 76 urges the cutter 37 into engagement with the inner surface of cone 62 over a portion of the cutter body. This is described below.

The cutter 37 can also be formed of the same, or similar material as the shaft 36. If desired, the complete cutting tool 35 can be milled or otherwise suitably formed of a single piece of material.

The cutter 37 is formed with one or more flutes 37b having sharp blade surfaces which rotate around and advance along the body of the cutter like the spiral of a screw thread. It is preferred that there be at least two flutes. The principal requirement of the flute or flutes is that they extend in front of and in back of the opening 64 during a complete cycle of rotation of tool 35 so that there always will be engagement of the blade surface of the flutes 37b with the cutting surface of the wall 65 surrounding the opening 64.

The operation of the instrument proceeds as follows. An incision is first made in the portion of the body into which the probe is inserted. The probe is then inserted through the opening. The motor 14 can be operated to energize the cutter tool 35 to cause the fluted blades of cutter 37 to rotate with respect to the shearing edges 65 of the opening 64.

Figure 4:
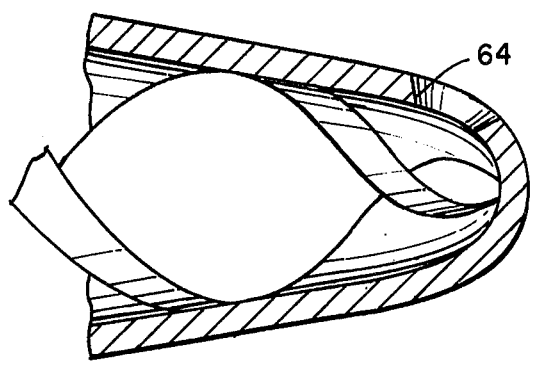
Figure 5:
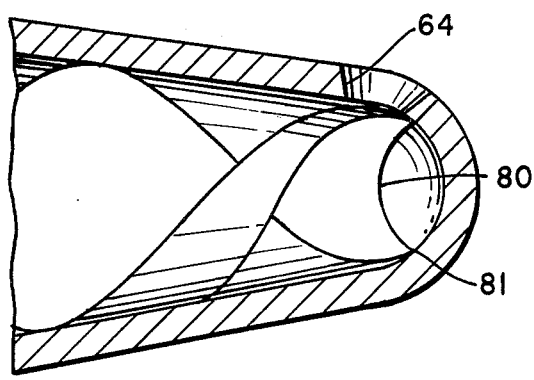
Figure 6:
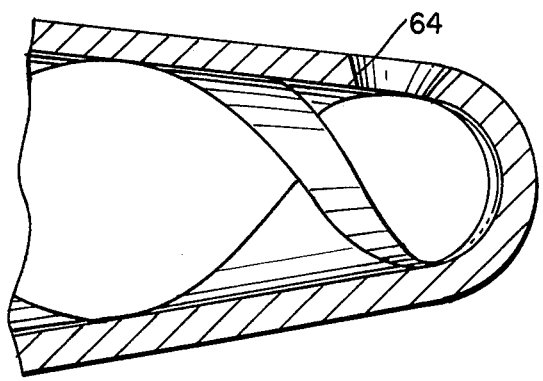

Evacuation force is applied through conduit 20 and the central passage to draw tissue into the opening 64. As the cutter 37 rotates, as shown in FIGS. 4–6, the flutes sweep across the opening 64. The outer diameter of flute of cutter 37 and the inner diameter of the nose cone are such that the flute's blades extend into the opening 64 as they sweep by. The spring 76 urges the tool 35 forward. The tissue caught between the edge of the cutter blade and the wall 65 of the opening 64 is carried along with the rotation of the flute until there is a shearing cut made between the blade and the wall. In this way, tissue is cut each time a blade passes under the opening 64 during each rotation of the tool 35.

The particles of tissue cut off and any fluid removed from the operating field are moved down the central passage 58 out through the conduit 20 into a collecting receptacle (not shown).

Irrigating fluid can be supplied from the conduit 22 through the outer passage 59 and out the opening 60. This can be done at the same time the tissue is being cut and removed from the operating field. The irrigating fluid can serve several functions. First of all, it can be supplied to an enclosed operating field, such as the eye, to compensate for removed fluid and tissue. This prevents the eye from collapsing. In addition, the irrigation fluid can be used to wash away or to position tissue within the generating field by suitably rotating the instrument. It also serves as a transporting means forming a suspension with the separated material.

A reverse flow fluid can be supplied through the conduit 24 into the central passage 58. It is sometimes desired to use this fluid to move particles which may have been trapped in the central passage 58 or in the cutter flutes 37b. One type of fluid control system for the suction, irrigation and reverse fluid flows is described in my copending application Ser. No. 208,282, filed Dec. 15, 1971, now U.S. Pat. No. 3,812,855 dated May 28, 1974, entitled "System for Controlling Fluid and Suction Pressure", which is assigned to the same assignee.

In the instrument shown in FIG. 2 of U.S. Pat. No. 3,945,375, a space is provided between the front end of the barrel-shaped cutter and the front end of the instrument tip. After a while the cutter blades wear down and, due to the spring biasing of the shaft, the cutter is moved forward towards the end of the tip. When the cutter is worn down to a point where the space is filled by the cutter body, a problem is then encountered in that the cutter body tilts or cocks causing the back portion of the body to contact the inner surface of the tip at a point. Stresses above the elastic limit of the cutter body material are produced and the structure is rapidly worn away or collapses. There is also excessive wear between the surface of the rotating blade and the inner surface 65 of the evacuation port which forms the stationary cutting surface. This excessive wear creates a gap between the two shearing surfaces thereby making the cutting less efficient and eventually impossible.

The cutter of U.S. Pat. No. 3,945,375 is generally conical in shape, that is, the diameter of the rear portion of the cutter body is greater than the diameter of the forward portion. Due to the difference in circumferential velocities at the different parts of a conical cutter body, caused by the difference in diameters, the wearing action of the larger diameter portion is greater than at the smaller diameter portion.

In the blade of FIG. 2 of U.S. Pat. No. 3,945,375, the edges of the blades have a constant width (surface area) throughout their entire length, that is, over the entire length of the cutter body going from the portion of greatest diameter to the portion of smallest diameter. This is shown best in FIGS. 3, 5 and 7 of the patent. Since the peripheral velocities along the length of the blade vary, increasing towards the rear, the wearing action is different.

Figure 3:
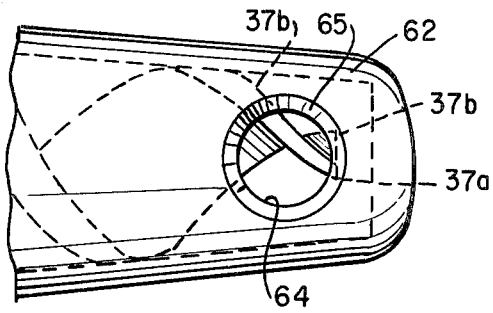
FIGS. 3–6 are fragmentary elevational views showing various embodiments of cutter bodies according to the invention.

In accordance with the subject invention, the width of the rotating cutter blades 37b varies from back to front of the cutter body. More particularly, as shown in FIGS. 2 and 3, the surface area of each blade 37b decreases going from the back (left) to the front (right) of the cutter body, as seen in FIG. 2. The amount of decrease in blade width (surface area) for maximum to minimum depends on the change in force normal to the surface of the blade that is required. In the embodiment of FIGS. 2–3, it is approximately about fifty percent. The percentage ratio can be virtually infinite if the tip of the cutter body comes to a point or is very small as in FIG. 4.

The cutting action of the cutter 37 of FIGS. 2 and 3 is the same as in U.S. Pat. No. 3,945,375. That is, as the blades sweep across the evacuation port 64, there is a two-point contact across the cutting surface 65 of the port. The cutter body is supported in the region to the rear of the evacuation port by by wider width blade surface 37b contacting the inner surface of the cutter tip.

By providing the larger surface area at the rearward end of the blade, a greater surface area is available for supporting the cutter body. Also, since there is a greater surface area, the amount of stress is decreased and with it the wear.

In general, it can be said that the wear of the cutter blade is a function of friction times the velocity of rotation of the cutter body times the stress. This is:

$$\text{Wear} = \mu(\text{coefficient of friction}) \times v(\text{velocity}) \times \sigma(\text{stress})$$

Stress is inversely proportional to the area of blade surface contact. By increasing the area of the supporting surface of the larger diameter portion of the body, which is rotating at a higher velocity, the stress is decreased. Therefore, assuming the same amount of friction and time, the total wearing is relatively constant throughout the length of the body.

The use of the variable surface area blade provides a further advantage in that it reduces the travelling space needed between the end of the cutter body and the front of the instrument tip because the stress on the body is controlled.

In the embodiment of FIGS. 2 and 3, the front end 37a of the cutter is flat and there is a small space between this tip and the inner surface 67 of the probe which is also shown as being flat. The inner surface also can be rounded. For cutting action it is only necessary that the end 37a of the cutter extend under the edge 65 of the port 64. The front end 37a of the cutter can be brought very close to the end 67 of the probe.

FIGS. 4, 5 and 6 show the front end of the front of the instrument tip 67 being curved in shape. The curved area can be, for example, a portion of a sphere. The front end 37a of the cutter body initially can be made very close to the inner end of the instrument tip. That is, since wear is reduced due to the use of the varying width blade supporting surface the requirement for additional travelling space for the cutter body is reduced at the front end of the tip to accommodate for blade wear and the pushing of the cutter body toward the tip of the instrument by the spring 76.

Since the requirement for travelling space on the tip is reduced, this means that the evacuation port 64 can be moved closer to the end of the tip of the instrument. In many cases, this is considered to be an advantage by a surgeon conducting an operation. As shown in FIGS. 2 and 3, the front end of the cutter body is made close to the end of the instrument tip. The leading edge of the port, closest to the tip end, has been made smaller than 0.016 inches.

In practice it has been found that the travelling space at the end of the instrument tip can be virtually eliminated if the varying surface area blade surface is provided so that the front end of the cutter body can make essentially a point contact with the inner surface of the instrument tip in the area in front of the stationary blade 64 at the evacuation port 65. This is shown in FIG. 4. This is so because with the reduced amount of blade contact surface area at the front end of the tip, there is a controlled amount of wear at the front end 37a of the cutter body. That is, as explained above, wear is a function of velocity. The peripheral velocity at the front end of the cutter body is relatively low, since the radius of the body there is small. There is basically a surface contact at the front end of the body which is a point, or small circular area, describing a circle of relatively small radius. The contact area should be such that the elastic limits of the cutter body are normally not exceeded. If and when this occurs, the blade portion is subjected to excess stress and would collapse. If the end 37a of the body wears, the body is pushed further forward toward the instrument tip end to an area where the blade surface area contact is wider thereby providing support and continuous contact with the shearing surface 65 surrounding the evacuation port 64. Utilizing this arrangement the evacuation port can be brought out substantially almost to the end of the instrument tip but above the center line so that there can be a shearing action.

FIG. 5 shows a preferred embodiment of the invention wherein the front end of the cutter body has been dished out at 80 so that effectively there is essentially a circumferential or peripheral contact of the front of the cutter body on a circular, or ring, surface at the front end of the instrument tip. That is, the area of wearing contact at the front end of the tip is only in the area 81, at the forward end of the cutter body where its surface surrounds the dished out region 80. The velocity of the cutter body in the area is relatively small, as compared to the supporting region at the rear of the body, since its radius is small. Therefore, there is reduced wear.

In each of the embodiments of FIGS. 4 and 5, where the end of the cutter body contacts the front of the probe, there is a microscopic wearing of the cutter body end at all times since the body is always being urged toward the probe end. This arrangement causes the cutter to be firmly and properly seated at all times.

It is also possible to provide a different type of front surface contact by making the radius of curvature of the cutter body slightly larger than the radius of curvature of the inner surface of the end of the instrument tip. This is shown in FIG. 6. Here, the end of the cutter body can be brought very close to the end of the tip. The support is as described with respect to FIGS. 2 and 3.

What is claimed is:

1. A surgical instrument for cutting tissue comprising a first tubular member having a tapered end portion, said end portion of said first tubular member formed with an opening therein for the tissue to enter to be cut, said first tubular member also formed with a shearing surface around at least a portion of the opening, a cutting tool within said tubular member, said cutting tool including a shaft having a cutter at one end and said cutter having a tapered body complementary to that of said end portion with at least one cutting surface formed thereon, means engaging said shaft for rotating said cutting tool, means for bringing the cutting surface of the cutter into positive engagement with the inner surface of said tubular member in the area of said shearing surface, said cutter cutting surface and said opening shearing surface providing a shearing action of the tissue in said opening as the cutter cutting surface sweeps across the opening, said cutter body having a supporting generally helical fluted surface extending for a substantial portion of the length of the cutter body and the width of a flute of said supporting surface, as determined in a direction parallel to the longitudinal axis of said shaft increasing going from said end of said first tubular member towards said shaft to distribute the wearing more equally along the length of the cutter body.

2. A surgical instrument as in claim 1 wherein there is a space between the front end of said cutter and the proximal end of the inner surface of the tapered front end portion of said first tubular member to provide a space for the cutter body to move as it wears.

3. A surgical instrument as in claim 2 wherein the end of said cutter terminates in front of the shearing surface of the opening of said first tubular member which is closest to the end of said tubular member.

4. A surgical instrument as in claim 1 wherein said means for bringing the cutter into positive engagement with the inner surface of the first tubular member comprises means acting on said shaft in a direction longitudinal of said shaft for urging the cutter toward the end of said first tubular member.

5. A surgical instrument as in claim 4 wherein the inner surface of the end of said first tubular member is closed, the front end of said cutter being shaped to contact said closed surface of the end portion in an area generally described by an arc.

6. A surgical instrument as in claim 5 wherein the portion of said cutter contacting said closed surface will wear away as the tool is used.

7. A surgical instrument as in claim 4 wherein the front end of said cutter is recessed to contact said end portion of said first tubular member beyond said cutting surface of said opening to produce a line type contact area.

8. A surgical instrument as in claim 7 wherein the portion of said cutter contacting said closed front surface will wear away as the tool is used.

9. A surgical instrument as in claim 4 wherein said means acting on said shaft produces a force normal to the inner surface of said first tubular member which is below the elastic limit of the material of the cutter body.

10. A surgical instrument as in claim 1 wherein the inner surface of the end of said first tubular member is curved and the front end of said cutter is also curved and spaced away from said inner surface.

11. A surgical instrument as in claim 1 wherein said cutter body is formed with a fluted cutting surface, which extends around the outer surface of the body and along at least a part of its length, said fluted cutting surface increasing in width from the front end toward the shaft end.

12. A surgical instrument as in claim 11 wherein the fluted cutting surface tapers to substantially a line at the front end of the cutter.

13. A surgical instrument as in claim 11 wherein said cutter includes a pair of said fluted cutting surfaces spaced substantially 180° apart with respect to said cutting tool.

14. A surgical instrument as in claim 13 wherein said means for bringing the cutter into positive engagement with the inner surface of the first tubular member comprises means acting on said shaft in a direction longitudinal of said shaft for urging the cutter toward the end of said first tubular member.

15. A surgical instrument as in claim 14 wherein the inner surface of the closed end portion of said first tubular member is closed, the front end of said cutter being shaped to contact said surface of the closed end portion in an area generally described by an arc.

16. A surgical instrument as in claim 15 wherein the portion of said cutter contacting said closed front surface will wear away as the tool is used.

17. A surgical instrument as in claim 14 wherein the front end of said cutter is recessed to contact said end portion of said cutter beyond said cutting surface of said opening to produce a line type contact area.

18. A surgical instrument as in claim 17 wherein the portion of said cutter contacting said curved front surface will wear away as the tool is used.

19. A surgical instrument as in claim 1 wherein said cutter body has a substantially zero clearance fit with the inner surface of said end portion of said first tubular member.

20. A surgical instrument as in claim 1 wherein said cutting surface of said cutter body comprises a blade and said blade having a portion which forms the supporting surface.

21. A surgical instrument as in claim 20 wherein the supporting surface is of a varying area such as to keep the stress-velocity product substantially constant along the length of the cutter body.

22. A surgical instrument as in claim 1 wherein said variable width supporting surface extends around and along the cutter body.

* * * * *